United States Patent [19]  
Numata et al.

[11] 3,985,818  
[45] Oct. 12, 1976

[54] METHOD FOR THE PREPARATION OF UNSATURATED DIMERS OF α-METHYLSTYRENES

[75] Inventors: Satoshi Numata; Tsutomu Takase; Yoshio Morimoto, all of Nagoya; Toshio Itakura, Okazaki, all of Japan

[73] Assignee: Mitsui Toatsu Chemicals, Incorporated, Tokyo, Japan

[22] Filed: Nov. 1, 1974

[21] Appl. No.: 520,151

[30] Foreign Application Priority Data
Nov. 9, 1973    Japan.............................. 48-125443

[52] U.S. Cl............................................. 260/669 P
[51] Int. Cl.² ........................................ C07C 15/12
[58] Field of Search .................... 260/669 P, 668 F

[56] References Cited
UNITED STATES PATENTS

| | | | |
|---|---|---|---|
| 2,593,417 | 4/1952 | D'Alelio | 260/669 P |
| 2,766,312 | 10/1956 | Sernuik | 260/669 P |
| 3,763,256 | 10/1973 | Massie | 260/669 P |

Primary Examiner—D. Horwitz  
Attorney, Agent, or Firm—Fisher, Christen & Sabol

[57] ABSTRACT

Unsaturated dimers which contain 2,4-diphenyl-4-methyl-1-pentene as their main component (i.e., in an amount of greater than 95%) are produced by reacting an α-methylstyrene at a temperature of from 20° to 100°C. in the presence of a sulfonic acid type cation-exchange resin catalyst and in the further presence of a primary or secondary monohydric alcohol containing from 2 to 5 carbon atoms. By this reaction, side products including a saturated dimer of 1,1,3-trimethyl-3-phenylindane, trimers and higher polymers are produced only in an extremely small amount. The unsaturated dimers are very useful as a molecular weight modifier when employed, instead of dodecylmercaptans, for the production of polymers such as an ABS resin, an AS resin, and the like.

10 Claims, 1 Drawing Figure

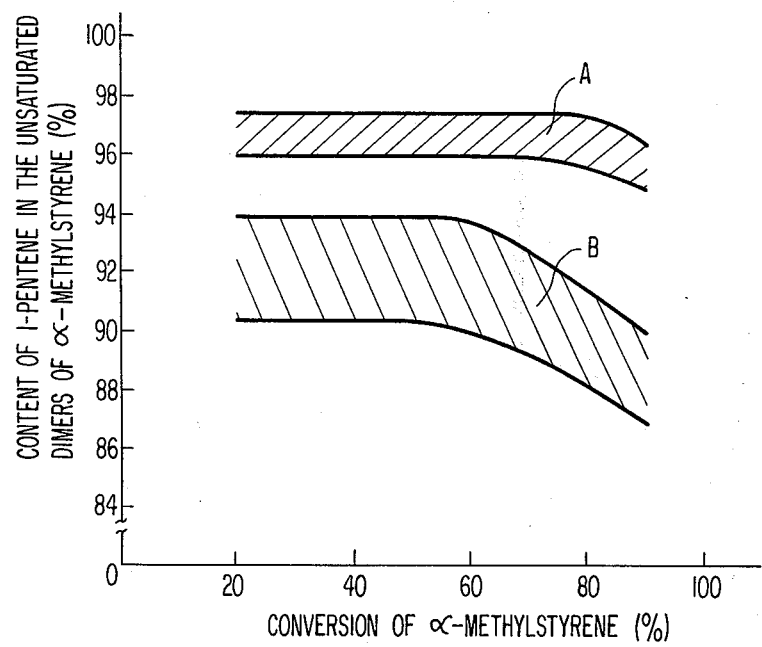

METHOD FOR THE PREPARATION OF UNSATURATED DIMERS OF α-METHYLSTYRENES

BACKGROUND OF THE INVENTION

1. Field of the Invention

This invention relates to a method for the dimerization of α-methylstyrenes. The α-methylstyrenes herein described are compounds having the following formula (I)

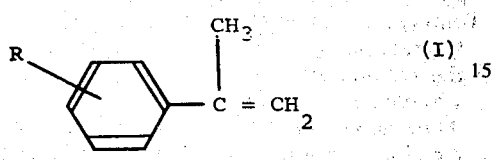

wherein R represents hydrogen or alkyl containing from 1 to 4 carbon atoms. The dimers of α-methylstyrenes include two kinds of unsaturated dimers, that is, 2,4-diphenyl-4-methyl-1-pentenes (hereinafter referred to simply as 1-pentenes) having the general formula (II)

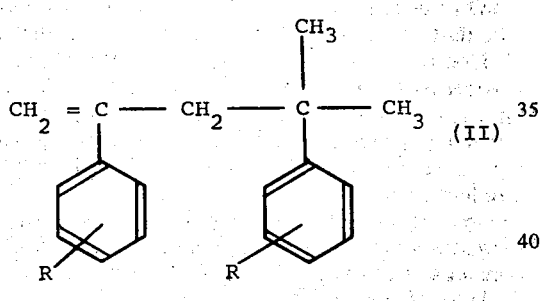

wherein R has the same meaning as defined in formula (I) above, and 2,4-diphenyl-4-methyl-2-pentenes (hereinafter referred to simply as 2-pentenes) having the general formula (III)

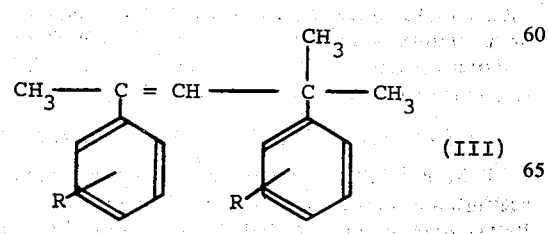

wherein R has the same meaning as defined in formula (I) above, and one kind of saturated dimers, that is 1,1,3-trimethyl-3-phenylindanes (hereinafter referred to simply as indanes) having the general formula (IV)

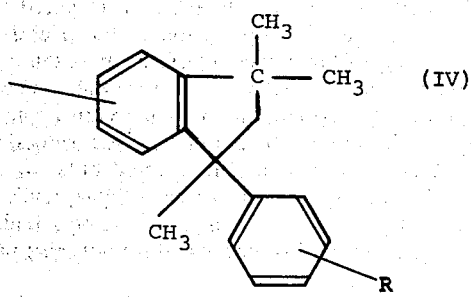

wherein R has the same meaning as defined in formula (I) above. More particularly, this invention rlates to a method for the preparation of unsaturated dimers of α-methylstyrenes which contain as their main component 1-pentenes expressed by the above-mentioned formula (II).

DESCRIPTION OF THE PRIOR ART

Unsaturated dimers of α-methylstyrenes, particularly 1-pentenes, are extremely useful as a molecular weight modifier for the production of polymers such as ABS resin, AS resin, polystyrene, SBR and the like.

Dodecylmercaptans have been heretofore used as molecular weight modifier for the above-mentioned polymers. In recent years, however, the use of dodecylmercaptans has been placed under limitation due to the problem of odor pollution, particularly of the offensive odor of dodecylmercaptans during handling and the residual odor in the polymer. Therefore, there is a strong demand for the provision of a molecular weight modifier which is free from toxity and offensive odor, and it has been found that 1-pentenes which are one of the unsaturated dimers of α-methylstyrenes are most excellent as said modifier. It is now highly desired to provide a method for producing these 1-pentenes with a high degree of purity.

Among unsaturated dimers of α-methylstyrenes, 1-pentenes are preferred as a molecular weight modifier while 2-pentenes are not preferred since the latter hinder the initiating reaction and accordingly require an undesirably longer induction period. Furthermore, indanes, α-methylstyrenes per se, and trimers or higher polymers of α-methylstyrenes are of no value as a molecular weight modifier. The unsaturated dimers of α-methylstyrenes useful as a molecular weight modifier are required not only to contain none of indanes, α-methylstyrenes and higher polymers thereof including trimers, but also to have a 1-pentenes content of 95% or more. This is due to the fact, as described hereinbefore, that 2-pentenes have properties undesirable for a molecular weight modifier. Hence, it is necessary that the unsaturated dimers contain 1-pentenes in an amount of 95% or more for use as a highly quality-controlled product exhibiting constant molecular weight-modifying ability.

However, the three kinds of dimers of α-methylstyrenes expressed by the afore-mentioned formulae (II), (III) and IV have boiling points close to each other when R is the same atom or group, so that separation of the useful dimers from the others by distillation is substantially impossible when they are mixed with each other. In addition, separation of the useful dimers is extremely difficult even by treatments other than distillation. Accordingly, it is an essential requirement to suppress the formation to a minimum of not only indanes, but also 2-pentenes in the production of the unsaturated dimers useful as a molecular weight modifier by the dimerization of α-methylstyrenes. Furthermore, the formation of higher polymers including trimers should be also suppressed for lowering production costs.

The production of unsaturated dimers of α-methylstyrenes has been proposed in Japanese Pat. No. 482072 (or Japanese Patent Publication No. 6335/1966) wherein there is used as a catalyst a mineral acid, an organic acid or a solid acid such as sulfuric acid, toluenesulfonic acid, silica gel, silica alumina, or the like. However, when a mineral acid or an organic acid such as sulfonic acid or toluenesulfonic acid is employed as catalyst for the production of the dimers, the ratio of 1-pentenes to the total of 1-pentenes and 2-pentenes (hereinafter referred to simply as the 1-pentene formation ratio) which are contained in the unsaturated dimers is substantially reduced and thus the dimer product is not preferred in quality as a molecular weight modifier. Further, the resultant dimer product disadvantageously contains a large amount of higher polymers including trimers. Moreover, the use of a mineral acid or organic acid undesirably requires an additional treatment such as washing with water or an alkaline solution after the dimerization reaction, with a large amount of effluent to be discharged. That is, even a trace of acid causes the isomerization of 1-pentenes to 2-pentenes during the distillation purification of the produced dimers. Accordingly, all acid must be completely removed prior to distillation when a mineral acid or organic acid is employed as catalyst. or solid acid catalysts such as silica gel or silica alumina have vital disadvantages in that the same have a short life time and that a relatively large amount of catalyst must be used for the production of the dimers, i.e., only several tens of grams of the unsaturated dimers is produced per gram of the catalyst. Furthermore, the 1-pentene formation ratio of the ultimate product is not satisfactory for use as a molecular weight modifier.

Further, Japanese Preliminary Patent Publication No. 44240/1973 describes a method wherein the dimerization reaction is carried out in the presence of a solid acid catalyst such as terra alba (acid clay), activated clay, silica alumina, a montmorillonite-type clay, silica gel, or the like, or a catalyst such as a cation-exchange resin coexisting with water or a polyhydric alcohol. However, even though the solid acid catalyst is employed in coexistence with water or a polyhydric alcohol, the above-mentioned disadvantages inherent to the solid acid catalyst cannot be overcome. On the other hand, when a cation-exchange resin is used as catalyst together with water or a polyhydric alcohol, some of the disadvantages involved in the use of the afore-mentioned mineral acid, organic acid or solid acid catalyst will be overcome, but there still remain the following disadvantages or problems to be solved.

One of the problems is that the 1-pentene formation ratio is still low. Particularly, the isomerization of 1-pentenes to 2-pentenes proceeds more easily as the conversion of α-methylstyrenes into the dimers proceeds to a greater extent, i.e., the 1-pentene formation ratio becomes lower with high conversion of α-methylstyrenes. The reason for this is not presently known, but it is assumed that an additive such as water or a polyhydric alcohol serves to reduce affinity with the catalyst as the reaction proceeds to a certain extent and is allowed to dissolve out in the organic material layer of the reaction system, so that the isomerizing activity of the catalyst increases to accelerate isomerization of 1-pentenes to 2-pentenes.

On the other hand, when water is used together with a cation-exchange resin catalyst, the reaction solution becomes heterogeneous due to the water. The starting α-methylstyrenes and water form an azeotropic mixture which is easily distilled out during the reaction, and it becomes difficult to maintain the reaction system in an equilibrium state. In this connection, even though the distilled water is permitted to return to the reaction system by use of a condenser, the equilibrium between water and the catalyst is destroyed, with the result that an uncontrollable reaction often occurs thereby producing a large amount of indanes as a result of intramolecular ring closure of unsaturated dimers of α-methylstyrenes.

On the other hand, when a polyhydric alcohol, particularly triethylene glycol, glycerine, or the like, is added for the production of the unsaturated dimers of α-methylstyrenes, the polyhydric alcohol has disadvantageously a boiling point approximating that of the reaction product and the separation of the reaction product from the alcohol is made difficult, resulting in reduction in purity of the product.

In order to overcome the prior art disadvantages, the present invention have developed a method for preparing unsaturated dimers of α-methylstyrenes in an industrially effective manner.

SUMMARY OF THE INVENTION

It is an object of the present invention to provide a method for the preparation of unsaturated dimers of α-methylstyrenes which contain 95% or more of 1-pentenes.

It is another object of this invention to provide a method for the preparation of unsaturated dimers of α-methylstyrenes wherein subsantially no indanes are produced and higher polymers including trimers are produced in only extremely small amounts.

Briefly, in accordance with the invention, there is provided a method for the preparation of unsaturated dimers of α-methylstyrenes wherein at leat one α-methylstyrene expressed by general formula (I) is reacted in the presence of a sulfonic acid type cation-exchange resin catalyst and in the further presence of a primary or secondary monohydric alcohol containing from 2 to 5 carbon atoms, and the reaction is carried out at a temperature ranging from 20° to 100 C.

BRIEF DESCRIPTION OF THE DRAWING

The sole FIGURE is a graphical representation of the relation between conversion of α-methylstyrene and the 1-pentene content of the unsaturated dimer product wherein the shaded area indicated by the letter A shows the range attained by the present invention and the shaded area indicated by the letter B shows the range of the comparative examples.

DESCRIPTION OF THE PREFERRED EMBODIMENTS

A suitable sulfonic acid type cation-exchange resin utilizable in the method of the present invention is a styrenedivinylbenzene copolymer carrying sulfo groups thereon and includes so-called gel-like resins (e.g. Dowex 50 wx produced by Dow Chemical Co.) and so-called porous resins (e.g. Ambelyst 15 produced by Rohm & Haas Co.).

Examples of the primary or secondary monohydric alcohols which are useful as an additive in the method of the invention and which contain from 2 to 5 carbon atoms are ethyl alcohol, isopropyl alcohol, n-butyl alcohol, sec-butyl alcohol, isobutyl alcohol, n-amyl alcohol, sec-amyl alcohol and iso-amyl alcohol. Methyl alochol and monohydric alcohols containing 6 or more carbon atoms cannot give satisfactory results with respect to the 1-pentene formation ratio. Methyl alcohol, for example, has a high vapor pressure and is readily distilled out of the reaction system during the reaction in the form of a vapor, so that it is very difficult to conduct the reaction operation in a stable manner. Hence, monohydric alcohols having one carbon atom and 6 or more carbon atoms are not suitable alcohols to be used as additives in the method of this invention. Furthermore, tertiary alcohols are not suitable for use in the present invention since the same are susceptible to dehydration in the presence of the catalyst, thereby forming olefins. The thus formed olefins in turn easily polymerize to produce oligomers. Thus, tertiary alcohols do not serve as an additive and, in some cases, may be converted into oligomers having boiling points approximating those of the unsaturated dimers of $\alpha$-methylstyrenes, resulting in difficulty in separation of the dimers from the reaction solution by distillation. Thus, tertiary alcohols are not suitable as the alcohol additive of this invention.

The reaction temperature practiced in the present invention is within the range of 20° to 100° C., preferably from +° to 80° 37 C. With temperatures lower than 20° C., the reaction velocity becomes very low and is inconvenient for practical application, whereas the use of reaction temperatures higher than 100° C. results in an increase of the vapor pressure of the alcohols and it accordingly becomes difficult to effect the reaction in a stable manner.

The method of this invention has a distinct advantage over the prior art methods in that the 1-pentene formation ratio of the unsaturated dimers of the $\alpha$-methylstyrene is extremely high, even with high conversions of the $\alpha$-methylstyrene. This is particularly illustrated by the drawing which shows the results of the dimerization of $\alpha$-methylstyrene and wherein the ordinate is expressed in terms of content of 1-pentene in the unsaturated dimers of $\alpha$-methylstyrene and the abscissa in terms of conversion of $\alpha$-methylstyrene. In the drawing, the results of the Comparative Examples (i.e., the shaded area indicated by the letter B) were attained by reacting an $\alpha$-methylstyrene in the presence of a sulfonic acid type cation-exchange resin catalyst with use, as an additive, of water, methyl alcohol, n-hexyl alcohol, n-octyl alcohol, ethylene glycol, diethylene glycol and glycerine, respectively. As will be apparent from the drawing, higher 1-pentene formation ratios can be attained even with high $\alpha$-methylstyrene conversion ranges by the method of this invention when compared with the methods of the Comparative Examples.

One aspect of the present invention is that the alcohol additive does not contaminate the final product. That is, after completion of the reaction, the added alcohol contained in the organic material layer can be substantially completely removed by distillation as the initial fraction and may be repeatedly used for reaction.

The cation-exchange resin catalysts used in he method of this invention are preferably sufficiently dried and used in a state substantially free from moisture. The amount of catalyst used is within the range of 0.1 to 50% by weight, and preferably from 0.2 to 10% by weight of the $\alpha$-methylstyrene employed. The alcohols used as additive may be added to the reaction system by mixing with the dried resin catalyst, or the alcohol and the resin catalyst may be independently introduced into the reaction system. The amount of the alcohol used is within the range of 20 to 500% by weight, and preferably from 60 to 200% by weight of the resin catalyst.

The reaction time is generally within the range of from 1 to 8 hours and the reaction velocity becomes greater with an increased amount of catalyst and with a decreased amount of the alcohol additive.

The $\alpha$-methylstyrenes useful in the method of this invention are the compounds of formula (I) wherein R is hydrogen or alkyl containing from 1 to 4 carbon atoms, and include, for example, $\alpha$-methylstyrene, m- or p-methyl-, ethyl-, propyl- or butyl- $\alpha$-methylstyrene, and the like. These $\alpha$-methylstyrenes may be used singly or in combination for producing co-dimers.

This invention will be particularly illustrated by way of the following examples and comparative examples wherein all parts are parts by weight unless otherwise stated.

EXAMPLES 1 – 5

A commercially available sulfonic acid type cation-exchange resin (Amberlyst 15, porous resin, produced by Rohm and Haas Co.) was washed with water to remove therefrom impurities of acidic matter, followed by drying at 100° C. for 10 hours under a reduced pressure of 5 mmHg absolute) to obtain a resin catalyst substantially free from moisture (less than 0.1%). 100 parts of $\alpha$-methylstyrene was mixed for dimerization at 60° C. with 2 parts of the resin catalyst and 2 parts of one of the alcohol additives shown in the following Table 1 including ethyl alcohol, isopropyl alcohol, n-butyl alcohol, iso-butyl alcohol and n-amyl alcohol. Each reaction was continued for about 5 hours, during which time samples were collected for analyzing the reaction solutions by gas-chromatography for determination of the conversion of $\alpha$-methylstyrene and the 1-pentene formation ratio. The test results are shown in Table 1 below. In every Example, there was produced no indane. The side products of higher oligomers including trimers at 70% conversion were produced in the amounts also shown in the Table.

Table 1

1-Pentene Formation Ratio* (%) for Different Conversions of α-Methylstyrene And Formation of Side Products At 70% Conversion

| Example No. | Additive | 1-Pentene Formation Ratio (%) under each Conversion of α-methylstyrene | | | | | Formation of Higher Polymers (Wt. % Based on Starting α-methylstyrene) at 70% Conversion |
|---|---|---|---|---|---|---|---|
| | | 20% | 40% | 60% | 70% | 85% | |
| 1 | ethyl alcohol | 97.2 | 97.2 | 97.8 | 97.1 | 96.4 | 2.2 |
| 2 | isopropyl alcohol | 97.4 | 97.3 | 97.2 | 97.0 | 96.8 | 1.5 |
| 3 | n-butyl alcohol | 96.9 | 96.8 | 96.9 | 96.5 | 96.0 | 2.5 |
| 4 | iso-butyl alcohol | 96.8 | 96.8 | 96.3 | 96.2 | 95.5 | 1.5 |
| 5 | n-amyl alcohol | 96.0 | 96.0 | 96.0 | 95.8 | 95.3 | 2.0 |

* $\dfrac{\text{Content of 1-pentene}}{\text{Total content of 1- and 2-pentene}} \times 100$ After completion of the reaction, the reaction solutions were respectively subjected to removal of the catalyst therefrom, followed by distillation. As a result, the purity (the total content of 1- and 2-pentenes) of the unsaturated dimers was found to be greater than 99.8% and any monohydric alcohol used as additives was not found in the products. The conversion data of Table 1 are shown in the drawing as the shaded area indicated by the letter A.

EXAMPLE 6

The procedure of Examples 1-5 was repeated using, instead of α-methylstyrene, a mixture of m- and p-methyl-α-methylstyrenes (having a mixing ratio of meta compound to para compound of 60:40). An analysis by gas chromatography of the resultant reaction solution after reaction of 4 hours at 60° C. revealed that the solution contained 19% by weight of unreacted monomers, 78% by weight of unsaturated dimers, and 3% by weight of higher oligomers including trimers. Furthermore, an N.M.R. analysis revealed that the unsaturated dimers contained 97.0% of 1-pentenes.

COMPARATIVE EXAMPLES 7 – 13

A commercially available sulfonic acid type cation-exchange resin (Amberlyst 15, porous resin, produced by Rohm & Haas Co.) was washed with water to remove acidic matter therefrom, followed by drying at 100° C. for 10 hours under a reduced pressure (of 5 mmHg absolute) to obtain a resin catalyst substantially free from moisture (less than 0.1%). 100 parts of α-methylstyrene was mixed for reaction with 2 parts of the resin catalyst and 2 parts of one of the additives shown in the following Table 2 including water, methyl alcohol, n-hexyl alcohol, ethylene glycol, diethylene glycol, triethylene glycol and glycerine. That is, the resin catalyst was added to a mixture of α-methylstyrene and additive with agitation. The reaction temperature was maintained at 60° C. During the reaction samples were collected for quantitatively determining by gas-chromatography unreacted α-methylstyrene, unsaturated dimers including 1-pentene and 2-pentene, and side products of indane, higher polymers including trimers. The conversions of α-methylstyrene (i.e., mole % of polymerized α-methylstyrene in terms of the starting α-methylstyrene) and 1-pentene formation ratios (i.e., percentage of 1-pentenes in terms of the total of 1-pentenes and 2-pentenes) were calculated from the above determinations.

The test results are shown in Table 2.

Table 2

1-Pentene Formation Ratio (%) For Different Conversions of α-Methylstyrene and Formation of Side Products At 70% Conversion

| Comparative Example No. | Additive | 1-Pentene Formation Ratio (%) under each Conversion of α-Methylstyrene | | | | | Formation Percentage (Wt. % Based On Starting α-methylstyrene) at 70% Conversion | |
|---|---|---|---|---|---|---|---|---|
| | | 20% | 40% | 60% | 70% | 85% | Indane | Higher Polymers Including Trimers |
| 7 | water | 92.8 | 92.8 | 92.9 | 92.0 | 90.4 | 3.5 | 8.0 |
| 8 | methyl alcohol | 90.9 | 90.9 | 90.4 | 89.6 | 88.2 | 2.7 | 7.3 |
| 9 | n-hexyl alcohol | 91.8 | 91.8 | 91.5 | 90.5 | 89.2 | Trace | 3.2 |
| 10 | ethylene glycol | 91.6 | 91.5 | 91.4 | 90.8 | 88.9 | Trace | 4.3 |
| 11 | diethylene glycol | 90.6 | 90.6 | 90.5 | 89.5 | 88.2 | Trace | 4.7 |
| 12 | triethylene glycol | 90.8 | 90.8 | 90.7 | 89.2 | 88.0 | Trace | 5.0 |
| 13 | glycerine | 91.6 | 91.4 | 91.4 | 90.3 | 88.5 | Trace | 4.9 |

The conversion data of Table 2 are shown in the drawing as the shaded area indicated by the letter B.

In Comparative Examples 12 and 13, the resultant reaction solutions were respectively subjected to removal of the catalyst therefrom, followed by distillation. As a result, it was found that the contents of 1-pentene and 2-pentene of the products, were 98.8% and 99.2%, respectively and polyhydric alcohol used as additive (i.e., triethylene glycol or glycerine) were found to be 1.0% and 0.6% respectively in the products.

What is claimed is:

1. A method for the preparation of 2,4-diphenyl-4-methyl-1-pentenes having the general formula

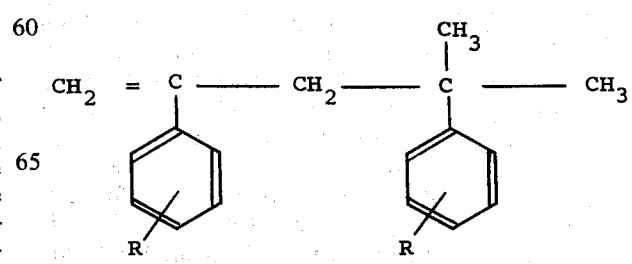

wherein R is hydrogen or alkyl having from 1 to 4 carbon atoms which comprises reacting α-methylstyrene having the general formula

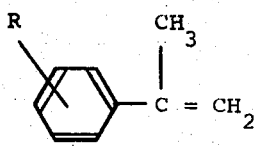

wherein R is the same as above at a temperature of from 20° to 100° C. in the presence of a sulfonic acid type cation-exchange resin catalyst and in the further presence of a primary or secondary monohydric alkanol which contains from 2 to 5 carbon atoms.

2. The method according to claim 1 wherein said secondary alkanol is isopropyl alcohol.

3. The method according to claim 1 wherein said α-methylstyrene is α-methylstyrene wherein R is hydrogen.

4. The method according to claim 3 wherein said secondary alkanol is isopropyl alcohol.

5. The method according to claim 1 wherein said reaction is carried out at a temperature of from 30° to 80° C.

6. The method according to claim 1 wherein said catalyst is present in an amount of from 0.1 to 50% by weight based on said α-methylstyrene.

7. The method according to claim 6 wherein said alkanol is present in an amount of from 20 to 500% by weight based on said catalyst.

8. The method according to claim 1 wherein said catalyst is present in an amount of from 0.2 to 10% by weight.

9. The method according to claim 8 wherein said alkanol is present in an amount of from 60 to 200% by weight.

10. A method for the preparation of 2,4-diphenyl-4 methyl 1-pentene which comprises reacting α-methylstyrene at a temperature of 30° to 80° C. in the presence of from 0.2 to 10% by weight based on said α-methylstyrene of a sulfonic acid type porous cation-exchange resin catalyst and from 50 to 200% by weight based on said catalyst of isopropyl alcohol.

* * * * *